(12) United States Patent
Alatriste

(10) Patent No.: US 6,202,784 B1
(45) Date of Patent: *Mar. 20, 2001

(54) STETHOSCOPE HAVING A LIGHT SOURCE

(76) Inventor: Anthony Alatriste, 8101 Canyon Lake Cir., Orlando, FL (US) 32835

( * ) Notice: Subject to any disclaimer, the term of this patent is extended or adjusted under 35 U.S.C. 154(b) by 0 days.

This patent is subject to a terminal disclaimer.

(21) Appl. No.: 09/304,251

(22) Filed: May 3, 1999

Related U.S. Application Data

(63) Continuation of application No. 09/060,895, filed on Apr. 15, 1998, now Pat. No. 5,989,186.

(51) Int. Cl.⁷ ........................................................ A61B 7/02
(52) U.S. Cl. ................................................................ 181/131
(58) Field of Search ........................................ 181/131, 137, 181/141

(56) References Cited

U.S. PATENT DOCUMENTS

| | | |
|---|---|---|
| 1,913,780 | 6/1933 | Wappler . |
| 2,566,687 | 9/1951 | Wehby . |
| 4,147,163 | 4/1979 | Newman et al. . |
| 4,580,198 | 4/1986 | Zinnanti, Jr. . |
| 4,783,813 * | 11/1988 | Kempka ................................. 381/67 |

* cited by examiner

*Primary Examiner*—Khanh Dang
(74) *Attorney, Agent, or Firm*—Holland & Knight LLP; David G. Maire; Robert L. Wolter

(57) ABSTRACT

A stethoscope having a light source includes a stethoscope head and flexible tubing coupled to the stethoscope head and in communication with ear pieces for the detection and transmission of sounds from a patient's body. A casing is affixed to a cover of the stethoscope head and has a light source mounted therein. A switch is operable mounted on the casing for activating and deactivating the light source. Notches extend intermediate the casing and cover for grasping the same during use. A first end of the casing is disposed toward a perimeter of the cover and has an aperture through which light is emitted. The first end is adapted for mounting thereon various instrument heads as an otoscope or opthalomoscope. The first end may extend beyond the perimeter of the cover for mounting thereon the instrument heads. In an alternative embodiment, the casing is detachably secured to the flexible tubing of the stethoscope.

19 Claims, 3 Drawing Sheets

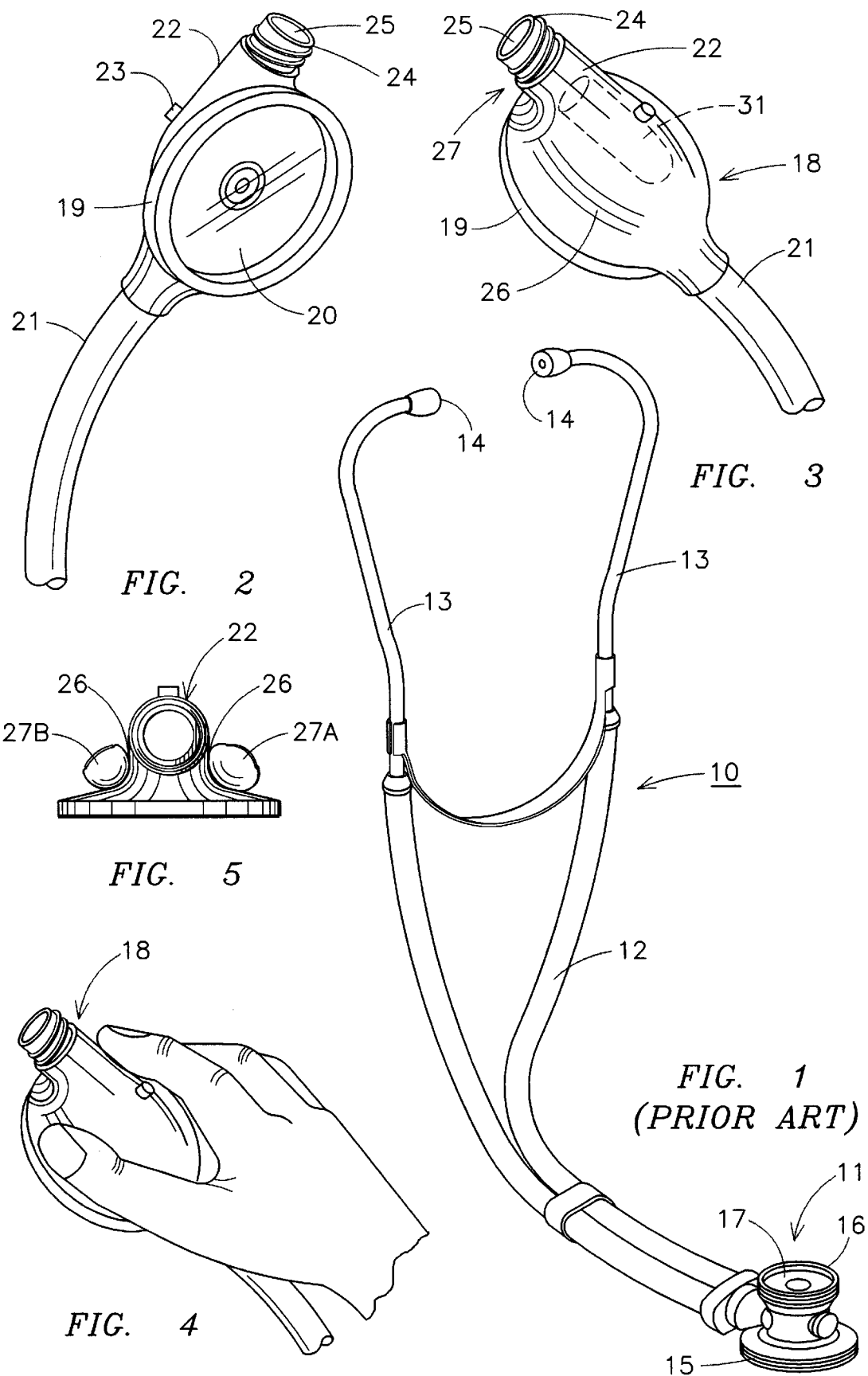

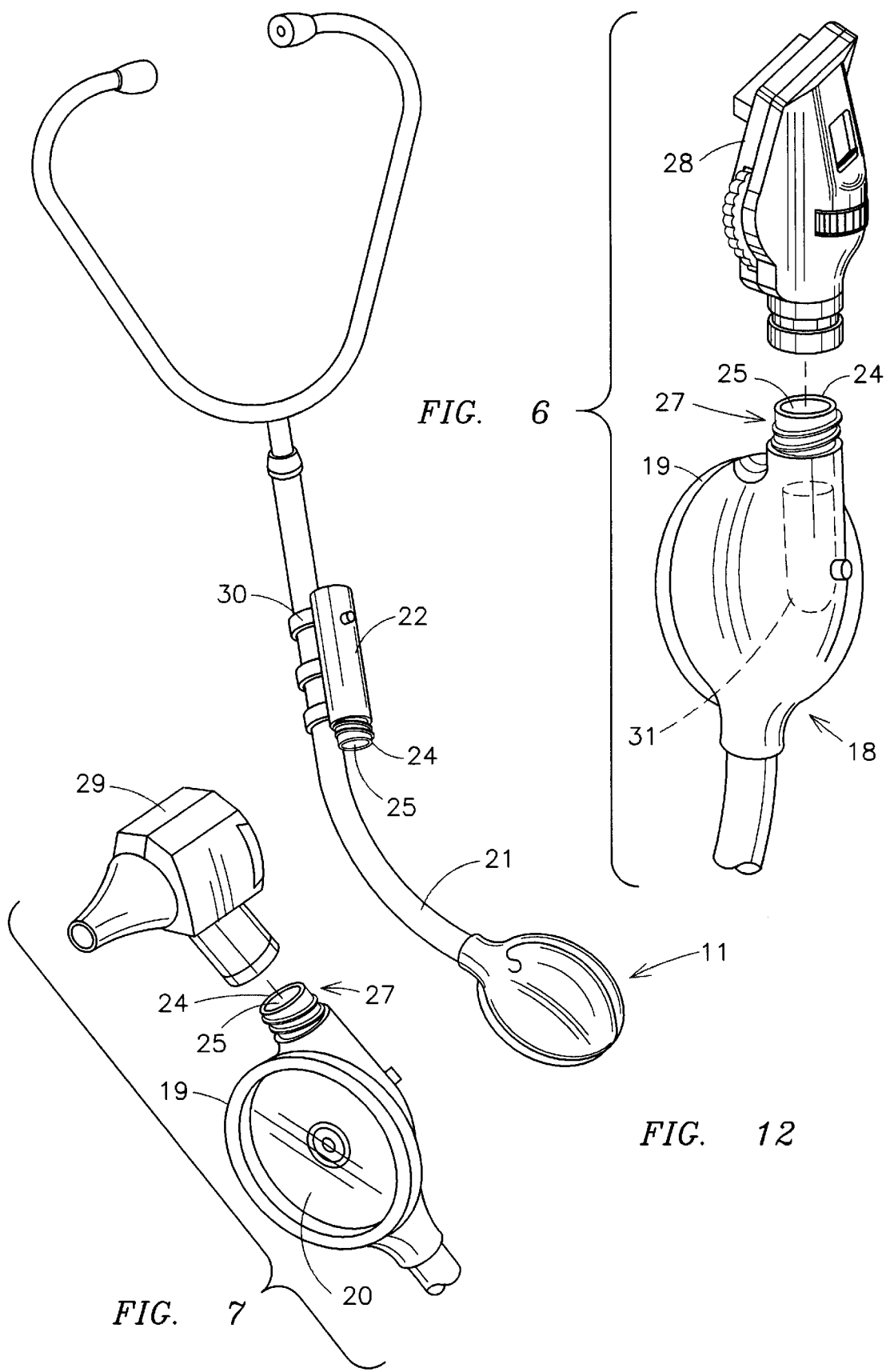

STETHOSCOPE HAVING A LIGHT SOURCE

This application is a continuation of the application U.S. Ser. No. 09/060,895, filed on Apr. 15, 1998, which has issued as U.S. Pat. No. 5,989,186.

FIELD OF THE INVENTION

This invention relates generally to instruments used by physicians, nurses, paramedics, and the like, for examination of patients. More specifically, this invention relates to stethoscopes adapted to provide multiple examination functions in addition to the conventional use of listening to involuntary and voluntary body functions.

BACKGROUND

Persons in the health care or emergency care industries, such as physicians, nurses, paramedics and the like, use various devices for examination of patients during the course of the day. One such instrument is a stethoscope which a user may carry with himself, or herself, by draping the stethoscope around his or her neck. The stethoscope is used to detect and listen to vibrations and sounds created from voluntary or involuntary body functions. In addition to the stethoscope, persons may use an opthalomoscope to examine the eyes of a patient, or an otoscope to examine the inner ear of a patient. A handle having a light source may be used; the opthalomoscope and otoscope heads are interchangeable on the handle.

In the emergency room environment, several nurses and physicians may use common ophthalmoscopes or otoscopes. These instruments may be stored at various examination stations. Ideally, a physician or nurse entering a particular examination station will use these instruments on a patient and then return the instrument to its storage place. Unfortunately, doctors and nurses may leave an examination station without returning the instruments to the appropriate storage place. A physician or nurse following this person does not have available the instrument necessary to conduct a proper examination of a patient.

SUMMARY OF INVENTION

Accordingly, it is an object of this invention to provide a single device or instrument that is adaptable to assist in several different patient examinations or tests. It is a further object of this invention to provide a stethoscope with a light source. Yet another object of this invention is to provide the light source on the stethoscope for throat examinations, and/or to have the light source capable of receiving an ophthalmoscope or otoscope head for eye and ear examinations.

These and other objects of the invention are achieved by mounting a light source on a stethoscope head, or on an area of the stethoscope so a user is capable of manipulating the light source to examine patients. A casing, for holding the light source may be fixed to the stethoscope head, and a notch is formed on each side of the casing intermediate the casing and stethoscope head. The notches provide a hand, or finger, receiving region for grasping the stethoscope head and casing. A first end of the casing is disposed toward a perimeter of the stethoscope head, and includes an aperture through which light from the light source is transmitted. The casing has a means, adjacent the first end of the casing, for receiving an otoscope and ophthalmoscope head. In addition, a switch is attached in communication with the light source to turn the light source on and off. In an alternative embodiment, the casing is detachably mounted to the tubing of the stethoscope by a uclamping means.

BRIEF DESCRIPTION OF THE DRAWINGS

FIG. 1 is a top perspective view of a conventional stethoscope having a dual head.

FIG. 2 is a bottom perspective view of the invention.

FIG. 3 is a top perspective view of the invention.

FIG. 4 is a top perspective view of the invention being held.

FIG. 5 is a front elevational view of the invention being held with by an index and fore finger of a user.

FIG. 6 is a perspective view of an opthalomoscope head being attached to the invention.

FIG. 7 is a perspective view of an otoscope head being attached to the invention.

FIG. 12 is perspective view of a second embodiment of the invention.

DETAILED DESCRIPTION OF THE DRAWINGS

Figure 8:
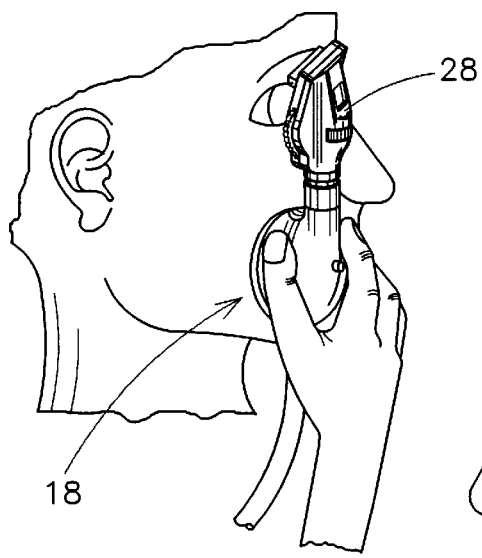
FIG. 8 is a perspective view of the invention with an opthalomoscope head attached thereon and used for examination of a patient.

A conventional stethoscope 10 is illustrated in FIG. 1, and includes a stethoscope head 11 flexible tubing 12, rigid conduits 13 attached to the flexible tubing 12; ear pieces 14 are attached to the conduits 13. The stethoscope 10 shown in FIG. 1 includes a bell portion 15 and diaphragm portion 16. Each of these portions 15 and 16 has an opening. A membrane 17 stretches across the opening of the diaphragm portion 16. The bell portion is applied to a patient to detect low frequency sounds created by such body functions as the flow of blood through arteries or veins; and the diaphragm portion 16 is used to detect high frequency sounds as air inhaled and exhaled from lungs, or murmurs in heart sounds. Each of the bell and diaphragm portions are generally bell shaped. A recessed area extends annularly on the stethoscope head 11 between the bell and diaphragm portions. A user grasps the stethoscope head 11 along the recessed area to manipulate the stethoscope head 11 during examination of a patient.

Other stethoscopes utilize a single head including only a diaphragm portion for detection of both higher and lower pitched sounds. When the stethoscope is placed against a patient's body slight pressure is applied to detect the same sounds as the bell portion of a dual head stethoscope. Pressure is applied more firmly in order to detect the same sounds as the diaphragm portion of the dual head stethoscope.

The present invention, generally illustrated in FIGS. 2 and 3, utilizes a single head stethoscope. The invention includes a stethoscope head 18 having a cover 19. A membrane 20 extends across an opening in the cover 19 and functions as a conventional stethoscope. A flexible tube 21 is coupled to the stethoscope head 18, and directs sounds transmitted from the stethoscope head to ear pieces.

A light source is mounted to the stethoscope on a region accessible for a user so the light is capable of being used for examination of a patient. In regard to FIGS. 2 and 3, the embodiment illustrated therein includes the light source affixed to the stethoscope head 18. A casing 22 is affixed on the stethoscope cover 19 and has a light source mounted therein for production of light during examinations. A switch 23 is operably mounted on the casing 22 in communication with the light source for tuning the light on and off.

A first end 24 of the casing 22 is disposed toward a perimeter of the cover 19, and includes an aperture 25 through which light is transmitted from the light source. The casing 22 shown in the embodiment herein has a longitudinal axis that is substantially parallel to the tube 21 attached to the stethoscope head 18 when the tube 21 has been straightened. The casing 22 may also be oriented on the stethoscope head 18 so the longitudinal axis is disposed at different angles with respect to the tube 21; however, the first end 24 on the casing 22 should be disposed on the stethoscope head 18 so a user may manipulate the casing 22 with the light source during examination with minimal interference from the tubing.

In regard to FIGS. 3 and 5, notches 26 extend longitudinally, with respect to the casing 22, intermediate the cover 19 of the stethoscope head 18 and the casing 22. The notches 26 serve as a means for grasping the stethoscope head 18 and the casing 22 to use either the light source or the stethoscope for examination. In FIG. 5, a forefinger 27A and index finger 27B are shown gasping the stethoscope head 18 along the notches 26. The stethoscope head 18 and casing 22 may also be held by grasping the casing along the notches 26 with the thumb and forefinger, as shown in FIG. 4. In the embodiment illustrated herein, the casing 22 is shown as integrally formed with the cover 19 as may be accomplished by manufacturing the cover 19 and casing 22 as a single piece, with the notches 26 extending there between.

Figure 10:
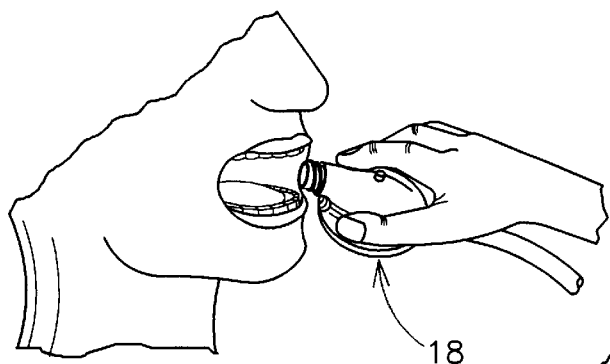
FIG. 10 is a perspective view of the invention used to examine the throat of a patient.
Figure 11:
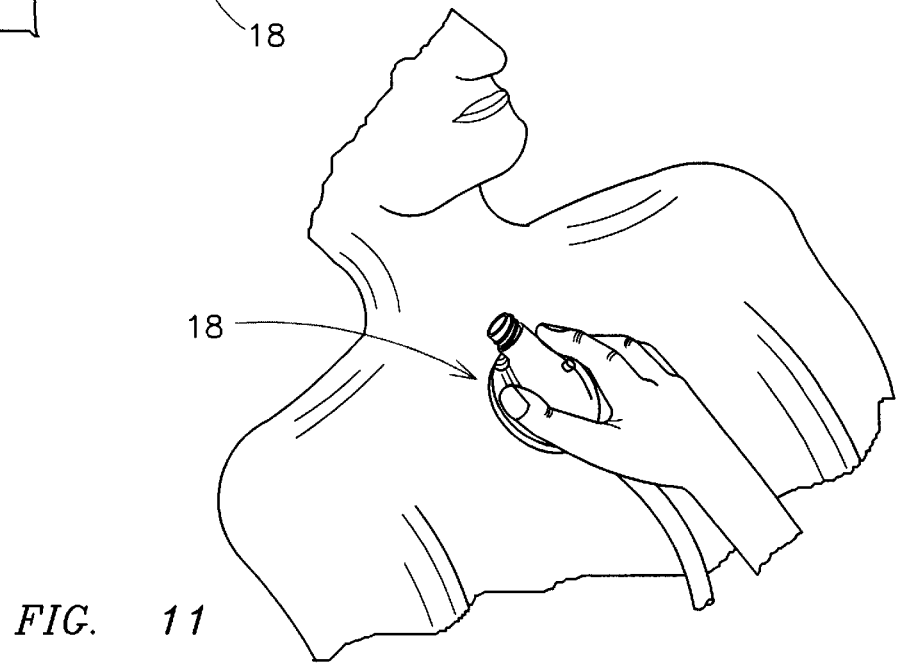
FIG. 11 is a perspective view of the invention used as a stethoscope.

The light source is mounted within the casing for emission of light through aperture 25 of the casing 22. The light source is limited in size and requires a casing of a corresponding size to avoid making the instrument to bulky to carry and use. The light source may include fiberoptic technology to provide a smaller size and adequate light to conduct examinations. The device, illustrated in FIGS. 10, is being used during examination of a patient's throat. The switch 23 is actuated to activate the light source. The light emanating from the casing 22 is directed into the throat by the user for observation of the patient. In regard to FIG. 11, a user grasps the stethoscope head 18 and casing 22 along the notches 26 for use of the stethoscope in a conventional manner.

In addition, to the uses of the invention as described above, the casing 22 may be adapted to receive various instrument heads. As noted above, the first end 24 of the casing 22 is disposed toward a perimeter of the cover 19. The cover 19 has a dome shape, or may have a bell shape, in which a surface of the cover extends away from the first end 24 of the casing 22. Thus, the first end 24 is spaced apart from the surface of the cover 19 sufficiently for attachment of an instrument head. The first end 24 of the casing 22 may extend beyond the perimeter of the cover 19, if necessary for attachment of instrument heads as described below in more detail.

The casing 22 includes means, adjacent the first end 24 of the casing, for attachment of instrument heads. The means for attachment illustrated in this specification includes a threaded portion 27 on an exterior surface of the casing adjacent the first end 24 of the casing 22. With respect to FIG. 6, an opthalomoscope head 28 is aligned for attachment to the casing 22; and in FIG. 7 an otoscope head 29 is aligned for attachment to the casing 22. Either one of these instruments 28 or 29 is equipped with a bottom threaded portion for mating relationship with the casing 22.

Figure 9:
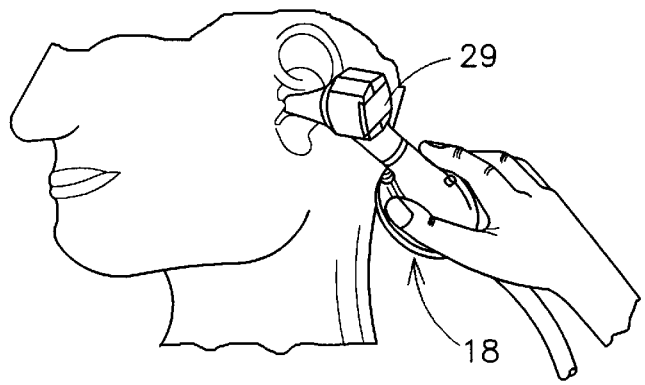
FIG. 9 is a perspective view of the invention with an otoscope head attached thereon and used for examination of a patient.

In use, when the stethoscope is held by a physician or nurse to examine the chest or back, the diaphragm is used as a normal stethoscope to detect sounds from the chest cavity. The light source may be turned on in order to examine the throat as shown in FIG. 10. With respect to FIG. 8, the opthalomoscope head 28 has been attached to the casing for examination of a patient's eyes; and in FIG. 9, an otoscope has been attached to the casing 22 for examination of a patient's ears.

An alternative embodiment is illustrated in FIG. 12 where the casing 22 is detachable secured to the flexible tubing 21. Clamps 30, affixed to the casing 22, grip the flexible tubing 21 to secure the casing 22 and the tubing 21. The clamps 30 may be equipped with a release mechanism to remove the casing from the tubing 21, by detaching the casing 22 with respect from the clamps 30, or the detaching clamps 30 from the tubing 21. Alternatively, the clamps 30 are resilient members that may be opened to detach the casing 22 from the tubing 21.

In use, the flexible tubing 21 is folded under the casing 22 and the user grasps the casing 22 with the tubing 21. The opthalomoscope or otoscope may be attached to the casing 22, if necessary. The light source is activated and used to examine a patient. The casing 22 may be removed for replacement of a new battery or light source, or for a new casing 22.

While I have disclosed the preferred embodiments of my invention, it is not intended that this description in any way limits the invention, but rather this invention should be limited only by a reasonable interpretation of the new recited claims.

What I claim as my invention is:

1. A stethoscope having a light source, comprising:
   (a) a stethoscope head having a cover and a membrane mounted within a perimeter of the cover extending across an opening in the cover, said membrane and opening on the stethoscope used for detection of sounds from voluntary or involuntary body functions;
   (b) a light source operably mounted on the stethoscope head within a casing affixed to said cover of said stethoscope head, said casing proximate to an exterior surface of said cover and having an aperture in a first end, said first end and aperture disposed along a periphery of the stethoscope cover through which light is emitted when said light source is activated for examination of a patient; and,
   (c) means, operably connected to the light source, for activating and deactivating said light source.

2. A stethoscope as defined in claim 1 wherein said stethoscope further includes a pair of notches extending substantially parallel a longitudinal axis of the casing, and said notches extending intermediate said casing and said stethoscope cover for grasping the stethoscope head for use during examination.

3. A stethoscope as defined in claim 1 wherein said stethoscope includes a an instrument head capable of being secured to the first end of the casing and means, on the casing adjacent said aperture, for receiving instrument heads for use in various examination functions.

4. A stethoscope as defined in claim 3 wherein said instrument head includes an opthalomoscope for examination of a patient's eyes.

5. A stethoscope as defined in claim 4 wherein said instrument head includes an otoscope head for examination of a patient's ears.

6. A stethoscope as defined in claim 5 wherein said stethoscope further includes a pair of notches extending substantially parallel a longitudinal axis of the casing, and said notches extending intermediate said casing and said stethoscope cover for grasping the stethoscope head for use during examination.

7. A stethoscope having a light source, comprising:
  (a) a stethoscope head having a cover and a membrane mounted within a perimeter of the cover extending across an opening in the cover;
  (b) a light source operably mounted on the stethoscope head within a casing affixed to said cover of said stethoscope head, said casing have an aperture in a first end, said first end and aperture disposed along a periphery of the stethoscope cover, and through which light is emitted when said light source is activated for examination of a patient, wherein said casing is affixed proximate to an exterior surface of the stethoscope cover such that said first end is spaced apart from said stethoscope cover and disposed in an orthogonal position with respect to said opening;
  (c) means, operably connected to the light source, for activating and deactivating said light source; and,
  (d) means, disposed on the first end of the casing, for receiving various instrument heads for use in communication with said light source and for examination of patients.

8. A stethoscope as defined in claim 7 wherein said stethoscope further includes a pair of notches extending substantially parallel a longitudinal axis of the casing, and said notches extending intermediate said casing and said stethoscope cover, for grasping the stethoscope head for use during examination.

9. A stethoscope as defined in claim 8 wherein said instrument head includes an opthalomoscope for examination of a patient's eyes.

10. A stethoscope as defined in claim 9 wherein said instrument head includes an otoscope head for examination of a patient's ears.

11. A stethoscope having a light source, comprising:
  (a) a stethoscope head having at least one membrane extending across an opening for detection of sounds originating from involuntary or voluntary body functions;
  (b) a flexible tube in communication with said stethoscope head, and means attached to the flexible tube distal the stethoscope head, for transmitting said sounds to a users ears;
  (c) a casing detachably secured to the flexible tubing, said casing having a light source mounted therein, said casing having a first end with an aperture through which light generated from said light source is transmitted; and,
  (d) means, mounted to said casing and engaging said flexible tubing, for detachably securing said casing to said flexible tubing.

12. A stethoscope as defined in claim 11 wherein said casing further includes means, extending along the first end of the casing, for receiving instrument heads for use in examination of patients.

13. A stethoscope as defined in claim 12 wherein said instrument head includes an opthalomoscope for examination of a patient's eyes.

14. A stethoscope as defined in claim 12 wherein said instrument head includes an otoscope head for examination of a patient's ears.

15. A stethoscope having a light source, comprising:
  a) a stethoscope head having a cover and an opening through which vibration or sound is detected; and,
  b) a light source operably mounted to said cover of the stethoscope head, and said light source adapted for receiving one of various instrument heads for examination of patients; and
  c) wherein said light source has a first end and an aperture along said first end disposed orthogonally with respect to said opening on said stethoscope head through which light is emitted, and said first end having means for receiving and securing said instrument heads thereon.

16. A stethoscope as defined in claim 15 wherein said instrument head is an opthalomoscope.

17. A stethoscope as defined in claim 16 wherein said instrument head is an otoscope.

18. A stethoscope as defined in claim 15, wherein the means for receiving and securing said instrument heads comprises a threaded portion formed on said first end.

19. A stethoscope as defined in claim 18 wherein said stethoscope further includes a pair of notches extending intermediate said casing and cover, and parallel to a longitudinal axis of the casing.

* * * * *